US009730649B1

(12) United States Patent
Jepsen

(10) Patent No.: US 9,730,649 B1
(45) Date of Patent: Aug. 15, 2017

(54) OPTICAL IMAGING OF DIFFUSE MEDIUM

(71) Applicant: OPEN WATER INTERNET INC., Sausalito, CA (US)

(72) Inventor: Mary Lou Jepsen, Sausalito, CA (US)

(73) Assignee: Open Water Internet Inc., Sausalito, CA (US)

( * ) Notice: Subject to any disclaimer, the term of this patent is extended or adjusted under 35 U.S.C. 154(b) by 0 days.

(21) Appl. No.: 15/264,088

(22) Filed: Sep. 13, 2016

(51) Int. Cl.
| | |
|---|---|
| A61B 5/01 | (2006.01) |
| A61B 5/00 | (2006.01) |
| H04N 5/33 | (2006.01) |
| G03H 1/04 | (2006.01) |
| G03H 1/22 | (2006.01) |
| A61B 8/00 | (2006.01) |
| A61B 8/08 | (2006.01) |

(52) U.S. Cl.
CPC ............ *A61B 5/745* (2013.01); *A61B 5/0042* (2013.01); *A61B 5/0075* (2013.01); *A61B 5/7264* (2013.01); *A61B 8/4416* (2013.01); *A61B 8/5261* (2013.01); *G03H 1/0443* (2013.01); *G03H 1/2294* (2013.01); *H04N 5/33* (2013.01); *G03H 2222/16* (2013.01)

(58) Field of Classification Search
CPC ..... A61B 5/745; A61B 5/0075; A61B 5/7264; H04N 5/33; G03H 1/0443; G03H 1/2294
See application file for complete search history.

(56) References Cited

PUBLICATIONS

Arridge, Simon R., Nonuniqueness in diffusion-based optical tomography, Optics Letters, Jun. 1, 1998, vol. 23, No. 11.
Hofmann, K. P., Differential Light Detector, Rev. Sci. Instrum., Feb. 1979, vol. 50, No. 2.
Eggebrecht, Adam T., Mapped distributed brain function and networks with diffuse optical tomography, Nat Photonics, Jun. 2014; 8(6): 458-464.
Freund, Issac, Memory Effects in Propagation of Optical Waves through Disordered Media, Physical Review Letters, Nov. 14, 1988, vol. 61, No. 20.
Goodman, J. W., Wavefront-reconstruction imaging through random media, Jun. 1966, Volum 8, No. 12, 311-313.
Harrach, Bastian, On uniqueness in diffuse optical tomography, Inverse Problems 25 2009, IOP Publishing Ltd.
Leith, Emmet N., Holographic Imagery through Diffusing Media, Journal of the Optical Society of America, Apr. 1966, vol. 56, No. 4.
Peng, Fenglin, Low loss liquid crystals for infrared applications, Liquid Crystals, 2014, vol. 41, No. 11, 1545-1552, Taylor & Francis Group.
Vellekoop, I. M., Focusing coherent light through opaque strongly scattering media, Optics Letters, Aug. 15, 2007, vol. 32, No. 16.
Yaras, Fahri, State of the Art in Holographic Displays: A Survey, Journal of Display Technology, Oct. 2010, vol. 6, No. 10, 443-454.

*Primary Examiner* — Mark Remaly
(74) *Attorney, Agent, or Firm* — Boswell IP Law; Aaron J. Visbeek

(57) ABSTRACT

A display pixel array is illuminated by infrared light in a frequency band. An infrared holographic imaging signal is generated by driving a holographic pattern onto the display pixel array. An image of an exit signal of the holographic infrared imaging signal is captured with an image pixel array. The image pixel array is configured to capture the infrared light and reject light outside the frequency band.

18 Claims, 11 Drawing Sheets

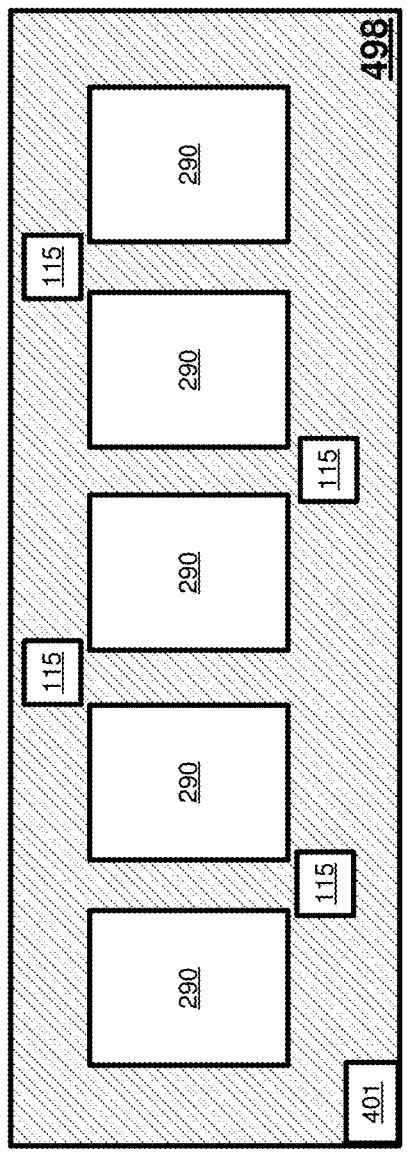
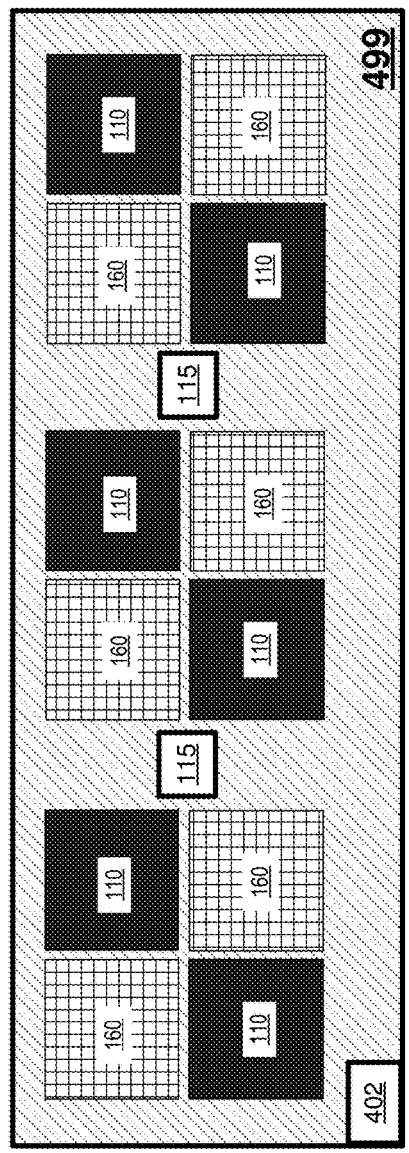
FIG. 4A
FIG. 4B

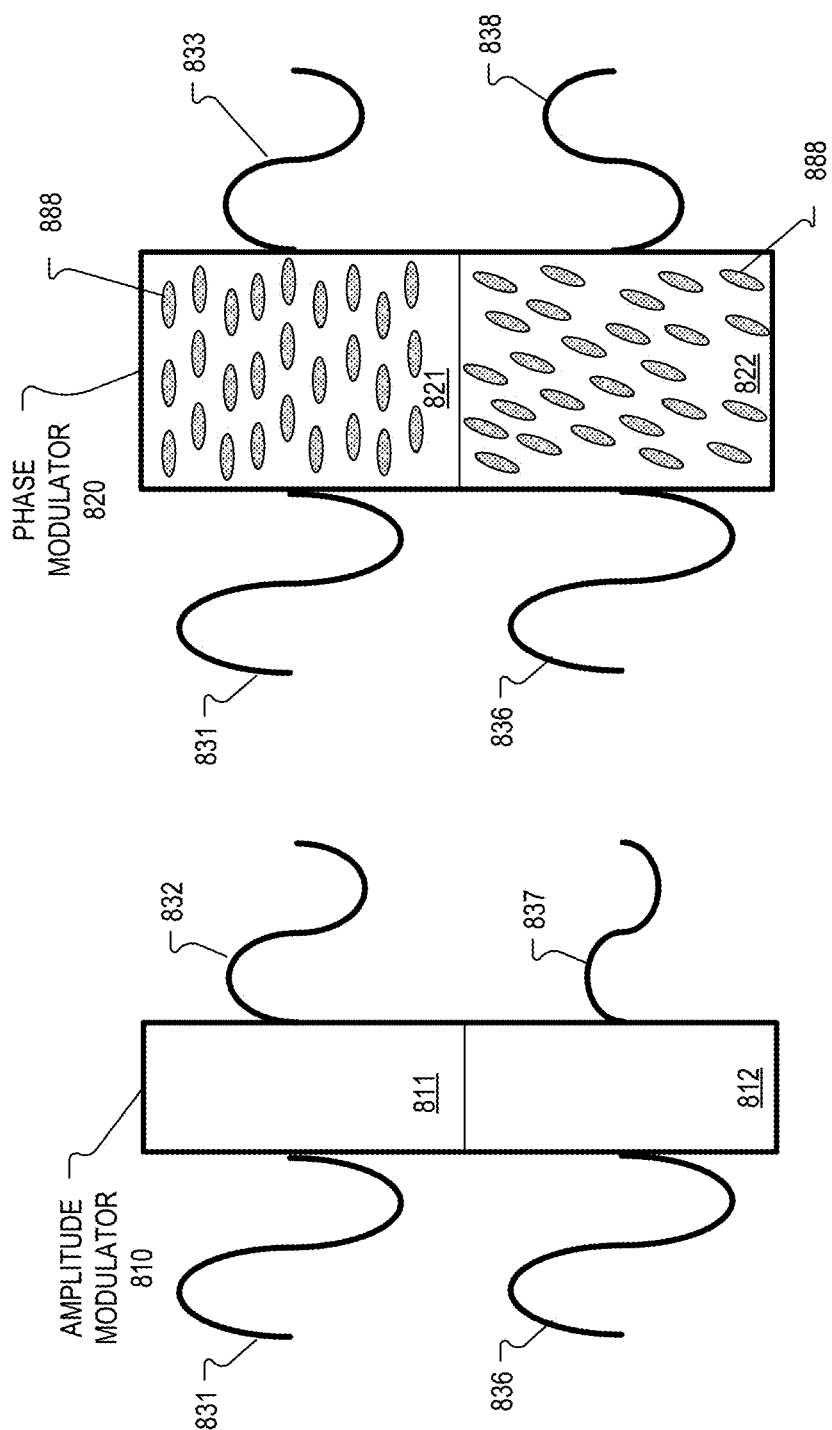

OPTICAL IMAGING OF DIFFUSE MEDIUM

TECHNICAL FIELD

This disclosure relates generally to imaging, and in particular but not exclusively to medical imaging using infrared light.

BACKGROUND INFORMATION

Rising healthcare costs put economic pressure on families and businesses in addition to constraining access to healthcare to those that can afford the increased cost. Some modes of medical imaging are large cost drivers in medical expenses since the systems and devices that facilitate the medical imaging are valued in the millions of dollars. As a result of the high price of some medical imaging systems, alternative testing and/or less accurate modes of medical imaging are standard-of-care, even though the more expensive medical imaging system is a better diagnostic tool. In developing nations, the high price of medical imaging systems such as MRIs (Magnetic Resonance Imaging) limits access to medical imaging because of both price and physical access since the sparse geographical distribution of medical imaging systems also imposes a travel barrier for those that would benefit from them.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIGS. 4A and 4B illustrate example form-factor implementations of a wearable imaging system, in accordance with an embodiment of the disclosure.

FIGS. 8A-8B illustrate example embodiments of displays for generating holographic infrared imaging signals, in accordance with an embodiment of the disclosure.

DETAILED DESCRIPTION

Figure 1:
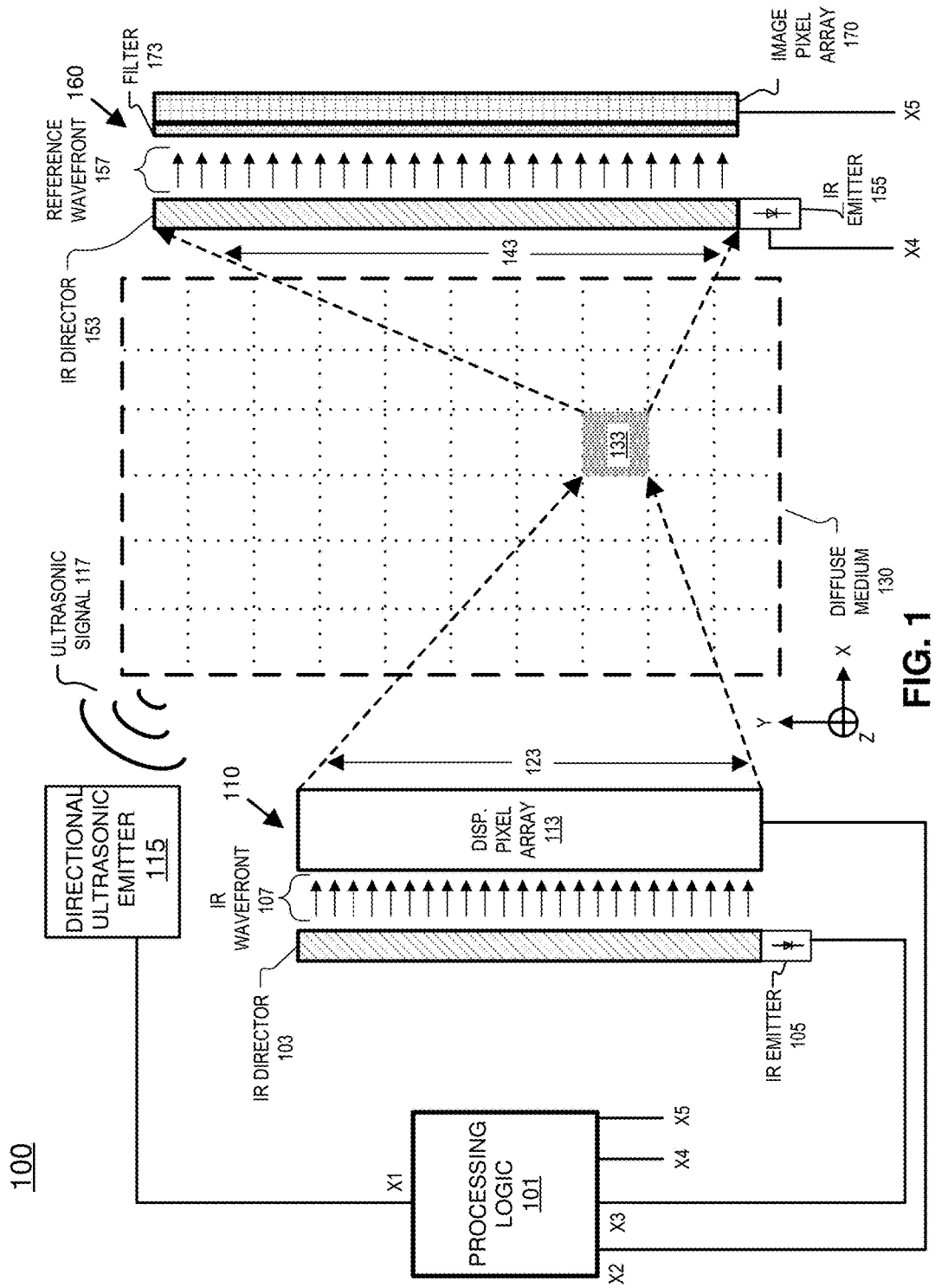
FIG. 1 illustrates an example imaging system that includes a display and an image pixel array, in accordance with an embodiment of the disclosure.

Embodiments of a system, device, and method for optical imaging of a diffuse medium is described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

The content of this disclosure may be applied to medical imaging as well as other fields. Human tissue is translucent to infrared light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue with near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least impeded (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is used at the detector; thus efficacy and power limitations as well as safety limits on input intensity limit TOF imaging resolution and utility. In contrast to TOF imaging, embodiments of this disclosure utilize a holographic beam to direct infrared light to a voxel of a diffuse medium (e.g. a brain or tissue). A light detector (e.g. image pixel array) measures an exit signal of the holographic beam. The exit signal is the infrared light of the holographic beam that is reflected from and/or transmitted through the voxel. The light detector may include a pixel array that measures the amplitude and determines the phase of the exit signal that is incident on the pixels. By capturing an image of the exit signal changes (e.g. oxygen depletion in red blood cells, scattering changes induced by potential differences in an activated neuron, fluorescent contrast agents and other optical changes) at a voxel or group of voxels in the diffuse medium, changes to that voxel or group of voxels can be recorded over time as the absorption, phase of scattering of the holographic beam varies with the changes in the tissues. Multiple voxels can be imaged by changing a holographic pattern on a display to steer the holographic beam toward the different voxels or groups of voxels. By raster scanning through many voxels (and recording the exit signals), a three dimensional image of the diffuse medium can be constructed.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise.

FIG. 1 illustrates an example imaging system 100, in accordance with an embodiment of the disclosure. Imaging system 100 includes processing logic 101, a display 110, and an image pixel array 170. In FIG. 1, imaging system 100 also includes a directional ultrasonic emitter 115 coupled to be driven by processing logic 101. In FIG. 1, display 110 includes an infrared emitter 105, an infrared director 103, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are less than 7 microns.

In one embodiment, display 110 is a holographic display. For the purposes of this disclosure, a holographic display includes a display where each pixel of the display can independently modulate the phase and intensity of light that illuminates the pixel. The array of pixels may utilize a transmissive architecture (e.g. modulating transmission through liquid crystal) or a reflective architecture (e.g. Liquid Crystal on Silicon).

Processing logic 101 may include a processor, microprocessor, cluster of processing cores, FPGA (field programmable gate array), and/or other suitable combination of logic hardware. Although not illustrated, system 100 may include a wireless transceiver coupled to processing logic 101. The wireless transceiver is configured to wirelessly send and receive data. The wireless transceiver may utilize any suitable wireless protocol such as cellular, WiFi, BlueTooth™, or otherwise.

In FIG. 1, display pixel array 113 is illustrated as a transmissive LCD that is illuminated by infrared wavefront 107. In the illustrated embodiment, infrared (IR) emitter 105 is coupled to be driven by output X3 of processing logic 101. When processing logic 101 turns on IR emitter 105, infrared light propagates into IR director 103. IR director 103 may be a light guide plate similar to those found in conventional edge lit LCDs. IR director 103 may be a slim prism utilizing TIR (total internal reflection). IR director 103 redirects the infrared light toward display pixel array 113. IR director 103 may include a sawtooth grating to redirect the infrared light toward IR display 113. IR emitter 105 is an infrared laser diode that emits monochromatic infrared light, in one embodiment. Monochromatic light may be defined as light within a 4 nm frequency band, for example. IR emitter 105 in one embodiment is pulsed, and in another embodiment is CW (continuous wave). The infrared light that IR emitter 105 emits may be centered around a frequency in the 700-1000 nm range. In one embodiment, the infrared light that IR emitter 105 emits may be centered around a frequency in the 1600-1700 nm range. In one example, emitter 105 generates monochromatic light centered around 850 nm.

Steerable infrared beams can be generated by display 110 by driving different holographic patterns onto display 110. Each different holographic pattern can steer (focus) the infrared light in a different direction. The directional nature of the infrared beam is influenced by the constructive and destructive interference of the infrared light emitted from the pixels of display 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. In one embodiment, the pixel size of display 110 approximates the wavelength of light illuminating the display. The pixel size may be 1 micron, although in some embodiments pixels sized up to 10 times the wavelength of light can be used. In one example, if IR emitter 105 is an 850 nm laser diode, the pixel size of display 110 may be 850 nm. The pixel size influences the angular spread of a hologram since the angular spread is given by the Grating Equation:

$$\sin(\theta)=m\lambda/d \qquad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the x and y dimensions of the pixel array.

In FIG. 1, system 100 includes an ultrasonic emitter 115. Ultrasonic emitter 115 is configured to focus an ultrasonic signal to a point in three-dimensional space. In the medical context, the ultrasonic emitter 115 is configured to focus an ultrasonic signal to a voxel within the human body. The voxel may be within the brain, abdomen, or uterus, for example. Focusing an ultrasonic signal to a given voxel of tissue creates a (temporary) localized compression zone at the voxel. In turn, the localized compression zone affects the propagation of infrared light through the localized compression zone. In particular, the phase of infrared light is modulated as a result of the localized compression of the tissue. As will be discussed in more detail below, the change of phase at the localized compression zone can be measured in a way that assists imaging tissue, or other diffuse mediums. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example.

Imaging module 160 is positioned to image exit signal 143, in FIG. 1. As infrared holographic imaging signal 123 propagates through diffuse medium 130 and at least a portion of it propagates through voxel 133 and exits diffuse medium 130 as exit signal 143. Exit signal 143 is a transmission signal in that imaging module 160 is imaging the transmission of infrared holographic imaging signal 123 through voxel 133. Reflective transmission signals (the reflection of holographic imaging signal 123 from voxel 133) may be measured in other embodiments.

Imaging module 160 includes IR emitter 155, IR director 153, and image pixel array 170. IR emitter 155 is coupled to receive an activation signal from processing logic 101 by way of output X4. IR emitter 155 emits an infrared light that shares the same characteristics as the infrared light emitted by IR emitter 105. IR emitter 105 and IR emitter 155 may be identical emitters. In one embodiment, instead of having separate emitters for IR emitter 105 and IR emitter 155, fiber optic lines direct infrared light from a shared IR emitter to IR director 103 and IR director 153. In this embodiment, when processing logic 101 activates the IR emitter, the infrared light emitted by the IR emitter travels through the fiber optics to illuminate both IR director 103 and 153. IR director 153 redirects the IR light emitted by IR emitter 155 toward image pixel array 170 as reference wavefront 157. IR emitter 155 paired with IR director 153 is one example of a reference wavefront generator for generating reference wavefront 157. IR director 153 may be made from a transparent plastic or glass such that IR director 153 is transparent to (or distorts in a known way) exit signal 143 that encounters IR director 153. IR director 153 may include a diffractive grating that is tuned to redirect the infrared light from IR emitter 153 toward image pixel array 170. The diffractive grating can be embedded within a transparent material of the IR director 153 so that it redirects a specific wavelength of IR light received from a particular angle (e.g. same angle as the IR emitter 155 is positioned) but is otherwise transparent to (or distorts in a known way) exit signal 143 since exit signal 143 is not incident upon the diffractive grating at the same angle as the IR light emitted by IR emitter 155. In one embodiment, IR director 153 includes a light guide plate as used in most liquid crystal display systems.

In the illustrated embodiment, an infrared filter 173 is disposed between IR director 153 and image pixel array 170. Infrared filter 173 passes the wavelength of infrared light emitted by IR emitters 105 and IR emitter 155 and rejects other light wavelengths that image pixel array 170 is sensitive to. Infrared filter 173 may be a bandpass filter with a bandwidth of four nanometers centered around the frequency of monochromatic IR light emitted by emitters 105 and 155. Although not illustrated, a focusing lens may be disposed between image pixel array 170 and IR director 153. The focusing lens may be configured to focus reference wavefront 157 and exit signal 143 such that the interference patterns of reference wavefront 157 and exit signal 143 are well focused on pixels of image pixel array 170 such that there is sufficient resolution for analysis of the interference patterns.

Image pixel array 170 may be implemented with an a-Si (amorphous Silicon) thin film transistors, in some embodiments or a CMOS (Complimentary Metal-Oxide-Semiconductor) image sensor, in some embodiments. Image pixel array 170 can be a commercially available image sensor, or optimized for detecting differences in signal rather than the maximum dynamic range of the signal, as for example as shown in by K. P. Hofmann and D. Emeis "Differential Light Detector" Rev. Sci Instrum 50, 249 1979, or in the case of detecting the change of holographic fringe patterns use processing logic 101 suited for detecting shifts in patterns.

The pixel resolution of image pixel array 170 may vary depending on the application. In one embodiment, the image pixel array 170 is 1920 pixels by 1080 pixels. In one embodiment, the image pixel array is 40 Megapixels or more. Some of the processing can be done in the image pixel array itself to enable lower bandwidth connections off chip. Image pixel array 170 can capture an infrared image of exit signal 143 by measuring the image charge generated in each pixel during a given integration period that is determined by an electronic shutter. The electronic shutter may be a global shutter (where each pixel measures the incident light during a same time period) rather than a rolling shutter. The electronic shutter can be actuated by processing logic 101 via input/output X5. Input/output X5 may include digital input/output lines as well as a data bus. Image pixel array 170 is communicatively coupled to processing logic 101 to send the captured infrared images to processing logic 101 for further processing. Image pixel array 170 may include a local (on-board) digital signal processor (DSP), in some embodiments, and processing logic 101 may receive the captured infrared images from the DSP.

In addition to capturing the amplitude of incident infrared light, the phase of incident infrared light can be determined from recording interference patterns using imaging module 160. The amplitude (intensity) of incident infrared light is measured by simply reading out the image charge accumulated in each photosensor (e.g. photodiode) of the pixels of image pixel array 170. The phase of light from exit signal 143 can also be measured by activating IR emitter 155 during the integration period of pixels of image pixel array 170. Since exit signal 143 is the same monochromatic wavelength as reference wavefront 157, the light interference of the exit signal 143 and the reference wavefront 157 indicates the phase of the infrared light of exit signal 143. The interference patterns created by the interference of exit signal 143 and reference wavefront 157 will be recorded by the image pixel array 170. The interference patterns can be analyzed to determine the phase of exit signal 143. The phase of and/or amplitude of different exit signals 143 can be analyzed to determine a suitable holographic pattern to image a given voxel (e.g. voxel 133).

One example process of linking a holographic pattern for driving onto display 110 to a given voxel utilizes directional ultrasonic emitter 115. To start this example process of linking a preferred holographic pattern (for driving onto display 110) to a given voxel in a diffuse medium, image pixel array 170 may initiate two image captures when an initial holographic pattern is driven onto display 110. The first image capture measures the amplitude of exit signal 143 by measuring the infrared light from exit signal 143 interfering with the light from reference wavefront 157 while the directional ultrasonic emitter 115 of FIG. 1 is off and thus captures the exit signal 143 with no phase change induced in voxel 133 by ultrasonic emitter 115. The phase of exit signal 143 can also be determined by analyzing the amplitude of different pixel groups that show interference patterns of exit signal 143 interfering with reference wavefront 157. The second image capture measures the interference of reference wavefront 157 with exit signal 143 when directional ultrasonic emitter 115 is activated and focused on voxel 133. As with the first image capture, both the amplitude and phase of exit signal 143 can be determined from the second image capture. Since the ultrasonic signal 117 locally compresses voxel 133 and induces a phase change of light propagating through the voxel 133, the first image capture and the second image capture will be different when the holographic pattern that is driven onto display 110 propagates through voxel 133. When the difference between the first image capture and the second image capture is maximized (to an acceptable level), the holographic pattern driven onto display 110 can be said to best focused on voxel 133 and is the preferred holographic pattern and thus linked to the voxel. Therefore, after the difference between the first and second image capture with the initial holographic pattern driven onto display 110 is calculated, the initial holographic pattern may be iterated to determine if a second holographic pattern driven on display 110 generates an even greater difference (measured by amplitude and/or phase) between a first and second image capture. Signal 123 is altered by driving a different holographic pattern on display 110, via for example simulated annealing, to maximize the difference between the first image capture and the second image capture. The holographic pattern may be iterated many times while seeking the largest change between the first and second image capture. This technique is used to create a dictionary (i.e. lookup table) of holographic patterns (corresponding to input signal 123) to map to focus the light sequentially to each and every voxel and to enable raster scanning of the volume, one voxel at a time. The first and second image capture may occur successively, one immediately after the other, to limit any change in exit signal 143 between image captures due to changes in diffuse medium 130.

Figure 2:
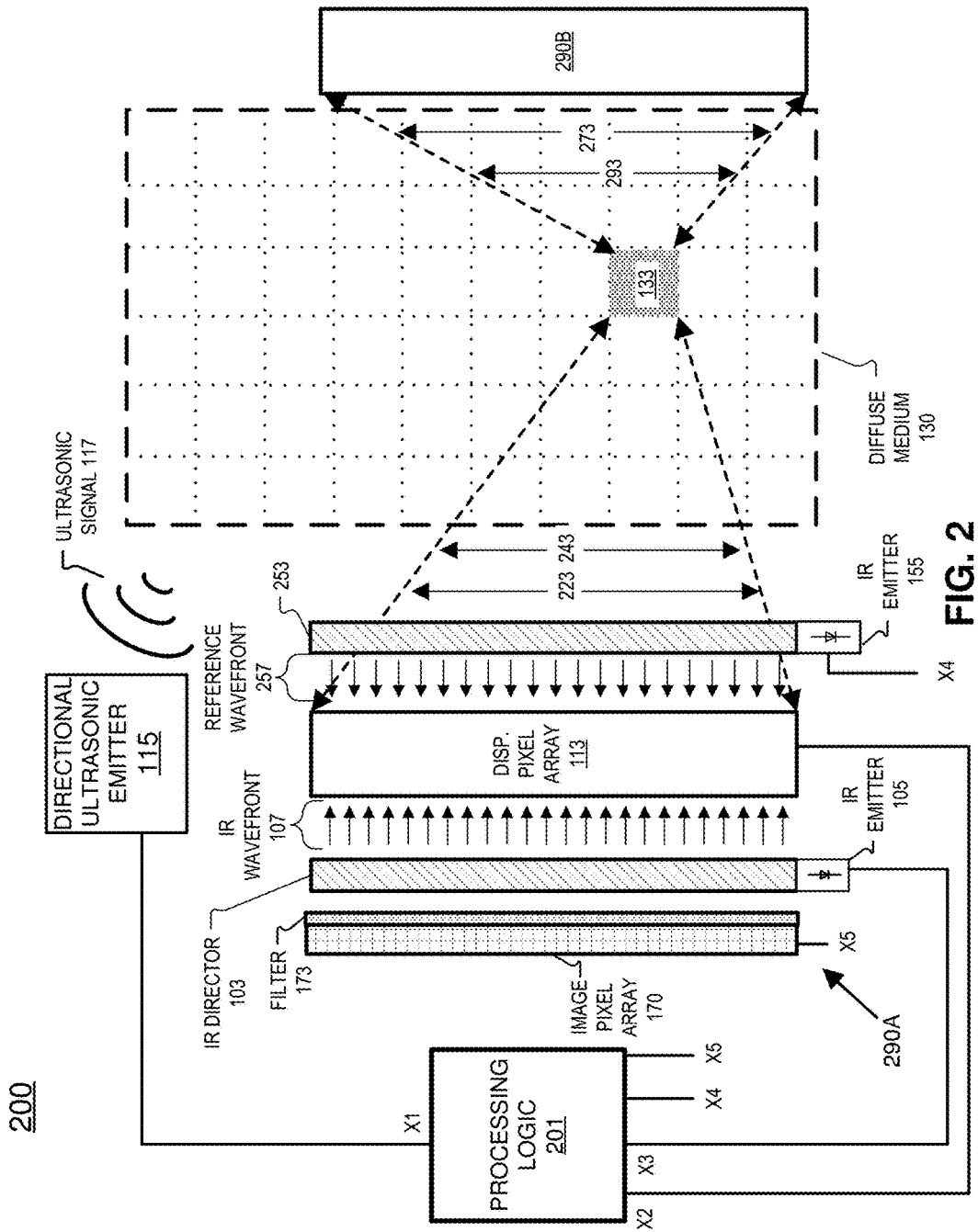
FIG. 2 illustrates an example imaging system that includes a display and an image pixel array, in accordance with an embodiment of the disclosure.
Figure 10:
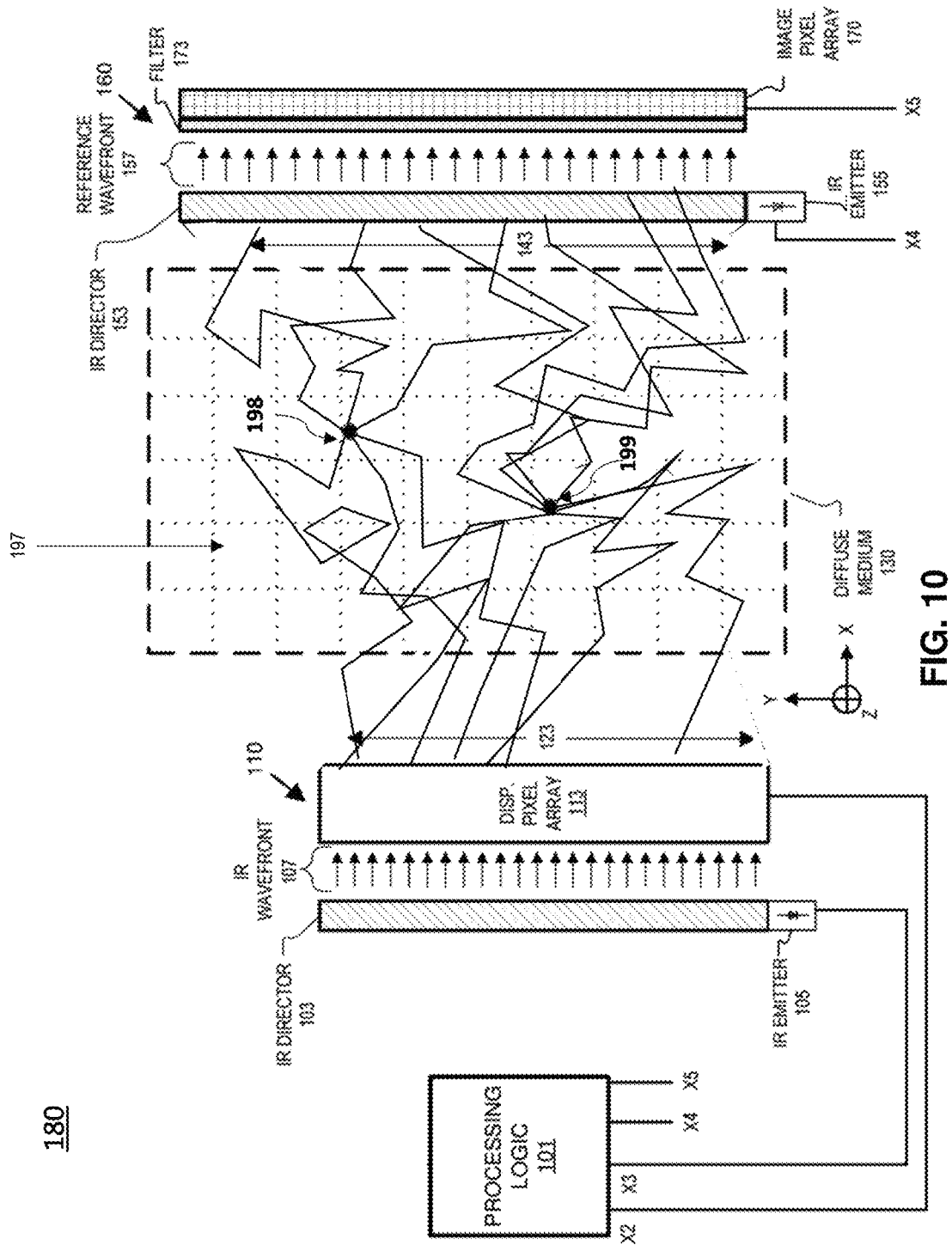
FIG. 10 illustrates an example imaging system that includes a display and an image pixel array, in accordance with an embodiment of the disclosure.

In system 180 illustrated in FIG. 10, imaging module 160 is positioned to image exit signal 143, similarly to in FIG. 1. However, system 180 of FIG. 10 does not include a directional ultrasonic emitter 115. Infrared holographic imaging signal 123 still propagates through diffuse medium 130 and exits diffuse medium 130 as exit signal 143. In FIG. 10, infrared holographic imaging signal 123 is depicted as light that is scattered by diffuse medium 130 while still propagating through the voxel(s) of interest. The scattered light paths of both signal 123 and 143 illustrated in FIG. 10 may be more realistic than the "clean" beams of FIGS. 1 and 2, illustrated for explanation purposes.

A process for linking a preferred holographic pattern (for driving onto display 110) to a voxel or a given set of voxels is different for system 180 since system 180 does not include directional ultrasonic emitter 115. For system 180, to start an example process of linking a preferred holographic pattern to a given set of voxels (two of this set are depicted as voxel 199 and voxel 198 in a diffuse medium 130 in FIG. 10), image pixel array 170 may initiate two image captures when an initial holographic pattern is driven onto display 110. The first image capture measures the amplitude of exit signal 143 by measuring the infrared light from exit signal 143 interfering with the light from reference wavefront 157 prior to application or presentation of stimulus 197 and thus captures the exit signal 143. The exit signal 143 may be analyzed for its amplitude alone or by signal 143 interfering with reference wavefront 157. The second image capture measures the effect of stimulus 197. The stimulus 197 is an internal change to a voxel or weighted group of voxels such that light is absorbed, phase retarded or scattered in a different way by that single voxel or group of voxels. In the brain such a change could be created by showing an image to a subject, playing some music to a subject, a request to a subject to think about something, or simply a wait for a change (internal bleeding, tumor growth, etc.) and other examples. Changes to blood that change the optical signal can be detected (deoxygenated blood absorbs light differently than oxygenated blood), blood volume itself can be detected and changes in its vasculature and flow, lipids, water, fat, melanin, and changes in scattering as can be seen in the direct firing pattern of neurons. Activity of neurons is characterized by ion and water fluxes across the neuron membrane inducing a change in membrane potential which can be seen by a change in light scattering as a function of neuron activity on the millisecond time scale. Fluorescent chemicals, nanoparticles placed via injection, injection or other means can also be used as beacons, including 2-photon systems and other methods where the wavelength of light is shifted at the voxel, area of interest or areas of interest. Many stimuli can impart optical changes inside the diffuse medium, these changes themselves, caused by the stimuli can be used as the beacons to tune the holographic image to focus on the region of change. The system can learn over time, akin to the way speech to text systems train on user's speech and grow continually better over time leveraging the data set and other implied and inferred data. Other existing anatomical data, or map data can be added to this model to extract more information and infer more information about the sites of interest. This work leverages techniques in machine learning, neural nets, deep learning, artificial intelligence and so forth.

With the stimulus present exit signal 143, as with the first image capture, both the amplitude and phase of exit signal 143 can be determined from the second image capture. With a stimulus 197 applied/presented for the second image capture, the first image capture and the second image capture will be different when the holographic pattern that is driven onto display 110 propagates through the multiple voxels affected by the stimulus 197. When the difference between the first image capture and the second image capture is maximized (to an acceptable level), the holographic pattern driven onto display 110 can be said to best represent delivering a measurement signal of the stimulus 197 and is the preferred holographic pattern and thus linked to a given stimulus. Therefore, after the difference between the first and second image capture with the initial holographic pattern driven onto display 110 is calculated, the initial holographic pattern may be iterated to determine if a second holographic pattern driven on display 110 generates an even greater difference (measured by amplitude and/or phase) between a first and second image capture. Signal 123 is altered by driving a different holographic pattern on display 110, via for example simulated annealing, to maximize the difference between the first image capture and the second image capture. The holographic pattern may be iterated many times while seeking the largest change between the first and second image capture. This technique is used to create a dictionary (i.e. lookup table) of holographic patterns (corresponding to input signal 123) to map to focus the light sequentially to each and every stimulus 197 and scanning of various stimuli.

Figure 7A:
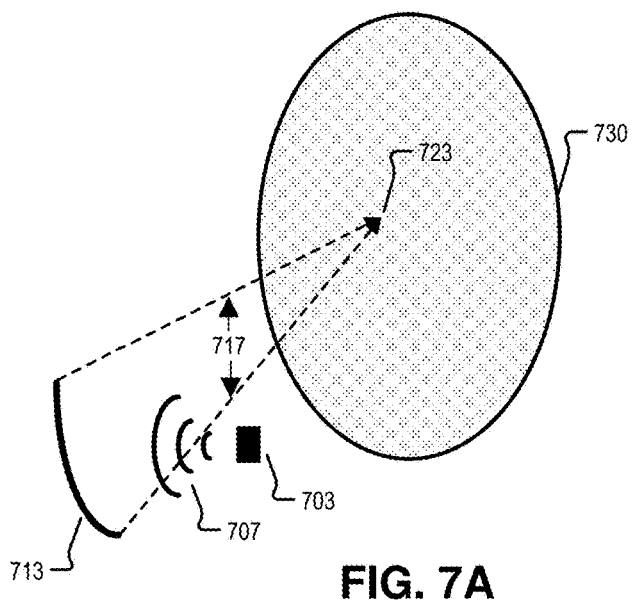
FIGS. 7A-7C illustrate example embodiments of a directional ultrasonic emitter, in accordance with an embodiment of the disclosure.
Figure 7B:
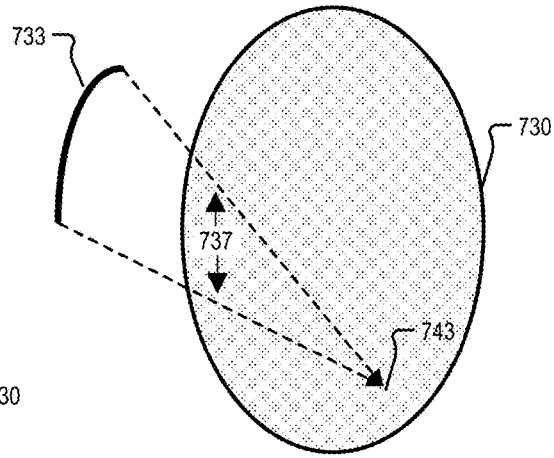
Figure 7C:
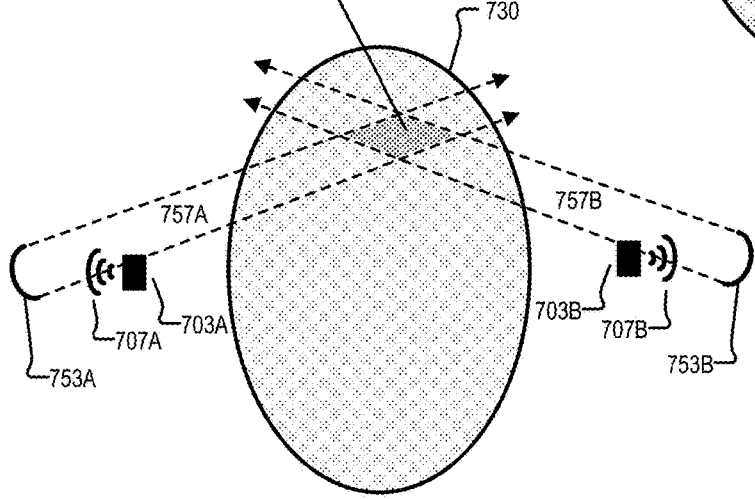

FIGS. 7A-7C illustrate example configurations of ultrasonic emitter 115. In FIG. 7A, directional ultrasonic emitter 115 includes a point source ultrasonic emitter 703 and an electronically controlled membrane 713. Point source ultrasonic emitter 703 is directed toward an electronically controlled membrane 713 that changes shape according to electronic input from processing logic 101. Changing the lensing shape of the membrane 713 electronically causes the ultrasonic signal 707 to be reflected and focused as beam 717 to the area of interest 723 in a diffuse medium 730. In one embodiment, the membrane includes polyvinylidene fluoride (PVDF).

In the embodiment illustrated in FIG. 7B, directional ultrasonic emitter 115 includes a piezo-membrane 733 that emits focused ultrasonic beam 737 to area of interest 747. Piezo-membrane 733 is a membrane having an array of regions and different electronic signals that drive the different regions. By selectively activating the different regions of the piezo-membrane 733, ultrasonic beam 737 can be focused on different points of interest 747 in diffuse medium 730. Piezo-membrane 733 may include polyvinylidene fluoride (PVDF).

FIG. 7C illustrates an additional embodiment of directional ultrasonic emitter 115. In FIG. 7C, the directional ultrasonic emitter includes two ultrasonic emitters. The first ultrasonic emitter includes point source 703A and moveable lens 753A. The second ultrasonic emitter includes point source 703B and moveable lens 753B. The first and second ultrasonic emitters are spaced apart from each other. The first ultrasonic emitter steers moveable lens 753A to direct an ultrasonic beam 757A with little divergence to the point of interest 763. Beam 757A propagates through point of interest 763, but is not focused on point of interest 763. The second ultrasonic emitter steers moveable lens 753B to direct an ultrasonic beam 757B with little divergence to the point of interest 763. Beam 757B propagates through point of interest 763, but is not focused on point of interest 763. The intersection of beams 757A and 757B create a local compression zone at point of interest 763.

The directional ultrasonic emitter 115 can be optionally used with IR display 113 to create a scanning look up table that links voxels in three-dimensional diffuse medium 130 with holographic patterns that can be driven onto IR display 113. This can also be achieved without the use of the directional ultrasonic emitter 115 as a beacon but instead through the use of other stimuli as described in [0033] and [0034].

FIGS. 8A-B illustrates an example side view of example pixels of a display pixel array that can be used as display pixel array 113. Display pixel array 113 may include amplitude modulation architecture 810 or a phase modulator architecture 820 or both. Amplitude modulator 810 functions similarly to conventional LCDs (modulating amplitude by adjusting voltage across liquid crystal pixel to rotate polarized light) except that the polarizers found in conventional LCDs are replaced with polarizers configured to polarize IR wavefront 107 and the liquid crystals are tuned to modulate infrared light. Amplitude modulator 810 can be solely used to modulate the amplitude of the signal and create the holographic wavefront 123 by creating diffractive slits for example. Phase modulator system 820 enables higher light throughput than modulator 810 by creating the same holographic wavefront 123 with better efficacy. Example light rays 831 and 836 may be part of infrared wavefront 107. Light ray 831 encounters pixel 811 and the amplitude of ray 831 is modulated to the amplitude of light ray 832. Similarly, light ray 836 encounters pixel 812 and the amplitude of ray 836 is modulated to the amplitude of light ray 837.

Alternatively, light ray 831 encounters pixel 821 and the phase of light ray 831 is modulated by pixel 821. Pixel 821 includes liquid crystals 888 disposed between two electrodes (e.g. indium tin oxide). A voltage across the electrodes changes the alignment of the liquid crystals 888 and the refractive index of the pixel 821 is changed according to the alignment of the liquid crystals 888. Thus, modulating the refractive index shortens or lengthens the optical path through the pixel 821, which changes the phase of the light rays 833 that exits pixel 821. In one embodiment, pixel 821 is configured so that applying a minimum voltage (e.g. 0V) across the electrodes of pixel 821 causes light ray 831 to not be phase shifted while applying a maximum voltage across the electrodes causes light ray 831 to be phase shifted 359°. Thus, applying voltages across the electrodes between the minimum and maximum voltages give full grey-scale control of phase shifting light ray 831 between 0° (zero radians) and 359° (almost $2\pi$ radians). To achieve this range, the optical path length of light ray 831 from the minimum to the maximum refractive index will need to differ by almost one full wavelength of the light (to achieve a phase shift of 359°). In one embodiment, the optical path length difference from the minimum refractive index is 850 nm to correspond with an 850 nm laser diode that generates infrared wavefront 107. To accommodate the thickness required to change the optical path length by almost a full wavelength, the thickness of phase modulator stage 820 may be thicker than a conventional LCD.

The illustrated embodiment of FIG. 8A shows that different modulation controls (e.g. voltages across the liquid crystal) are being applied to pixels 811 and 812 since the amplitude of light ray 837 exiting pixel 812 is smaller than the amplitude of light ray 832 exiting pixel 811. The illustrated embodiment of FIG. 8B shows that the phase of light ray 838 is adjusted $1\pi$ compared to the phase of light ray 833. As explained above, the phase of the light rays that propagate through pixels of phase modulator stage 820 can be modulated by adjusting the alignment of liquid crystals 888 to change the refractive index of the pixels in FIG. 8B. As illustrated, the alignment of the liquid crystals 888 in pixels 821 and 822 is different.

To generate a composite image of diffuse medium 130, multiple voxels of diffuse medium 130 can be imaged by imaging system 100 of FIG. 1. Prior to imaging each voxel, a focusing procedure may be performed to determine a suitable holographic pattern to image that voxel. In FIG. 1, three-dimensional diffusing medium 130 has an x dimension, a y dimension, and a z dimension (in to the page). The focusing procedure may start at a voxel having a coordinate of 1, 1, 1 and finish at a voxel having a coordinate of q, r, s, where q, r, and s are the number of voxels in each dimension x, y, and, z, respectively. The dimension of each voxel can be any dimension. In one embodiment, each voxel is 1 cm cubed. In on embodiment, each voxel is 1 mm cubed. Smaller voxels are possible.

In one example focusing procedure, display 110 generates a first probing infrared holographic imaging signal 123 by driving a first probing holographic pattern onto display 110. Imaging module 160 captures exit signal 143 in a first calibration infrared image. At a different time, directional ultrasonic emitter 115 is focused on a first voxel (e.g. 1, 1, 1) and imaging module 160 captures exit signal 143 again in a second calibration infrared image. The phase and/or amplitude difference between the first calibration infrared image and the second calibration infrared image is determined. As described above, the phase of the light from exit signal 143 may be determined by analyzing the interference patterns that are recorded in difference pixel groups of the calibration images. The amplitude of exit signals 143 can be determined simply from the image charge readings of each pixel. The determination of the phase and/or amplitude difference may be made by processing logic 101 and written to a memory on-board processing logic 101 or an auxiliary memory coupled to processing logic 101 (not illustrated). A difference value is then linked to the first probing holographic pattern.

Display 110 generates a plurality of probing infrared holographic imaging signals 123 (by driving different probing holographic patterns onto display 110) and records the amplitude and/or phase difference of exit signal 143 for each probing infrared holographic imaging signal between when the directional ultrasonic emitter 115 is and is not focused on the voxel of interest. In one example, fifty probing infrared holographic imaging signals are generated by fifty different probing holographic patterns being driven onto display 110. The fifty different holographic patterns may be random holographic patterns or may be fifty pre-determined holographic patterns that generate beam shapes that make good searching beams that would be well distributed throughout the diffuse medium. After the amplitude and/or phase difference for each probing infrared holographic imaging signal is recorded, a probing holographic pattern that yielded the largest amplitude and/or phase difference in exit signal 143 is selected. A new fifty probing infrared holography imaging signals are generated based on the selection and iteratively an optimum holographic imaging signal for a certain voxel is determined. As discussed above, focusing an ultrasonic signal on a voxel creates a local compression zone that alters the phase of infrared light propagating through the local compression zone. Altering the phase at the voxel will impact the phase of infrared light propagating through the voxel. Changing the phase at the voxel can also impact the amplitude of infrared light received by imaging module 160 since altering the phase at voxel 133 may cause infrared light to scatter differently. Thus, the selected probing holographic pattern that generated the largest phase difference (and/or amplitude difference) in exit signal 143 can be assumed to have best directed light to image pixel array 170 via the voxel of interest.

50 years ago in 1966 the Optical Society of American published an article entitled "Holographic Imagery through diffusing media" in the Journal of the Optical Society of America 56, 4 pg 523 authored by Emmett Leith and Juris Upatnieks. In the same years Joe Goodman et. al authored a paper published by the American Physical Society entitled "Wavefront-reconstruction imaging through random media" Applied Physics Letters, 8, 311-312 (1966). This work was re-popularized by the Optical Society of America when it published on Aug. 15, 2007 in article entitled "Focusing coherent light through opaque strongly scattering media." In this article and the aforementioned articles in this paragraph, the authors describe shaping a wavefront in order to focus the wavefront on a pre-defined target even as the shaped wavefront encounters a scattering medium on its path to the pre-defined target.

Although the contexts are different, infrared holographic imaging signal 123 can be shaped to "focus" on imaging module 160 even though it encounters a diffuse medium 130. The optical path from display 110 to imaging module 160 via voxel 133 is analogous to the "scattering sample" described by the authors of "Focusing coherent light through opaque strongly scattering media." The focusing procedure described in this disclosure is the process of shaping the holographic imaging signal displayed by display 110 to focus the holographic imaging signal on imaging module 160 while also propagating through a specific voxel (e.g. voxel 133).

Determining the selected probing holographic pattern that generates the largest phase difference in exit signal 143 may be a first stage of the focusing procedure for a given voxel. In one embodiment, a second stage of the focusing procedure includes a Simulated Annealing (SA) algorithm that includes iterating on the selected probing holographic pattern to generate a fine-tuned holographic pattern that generates an even greater phase change in exit signal 143 (the larger phase change indicating even more infrared light being focused on imaging module 160 via voxel 133) than the selected probing holographic pattern. In another embodiment, the second stage focusing procedure (using Simulated Annealing) can be used standalone without the first stage.

The selected probing holographic pattern for the voxel, or group of voxels is linked to the voxel or group of voxels if only the first stage of the focusing procedure is implemented. The fine-tuned holographic pattern is linked to the voxel or group of voxels if the second stage of the focusing procedure is implemented. The linked holographic pattern may be stored in a lookup table. The focusing procedure is repeated for each voxel of interest in diffusing medium 130. Hence, each voxel is linked to a preferred holographic pattern for that voxel that generates an infrared holographic imaging signal that is focused on the particular voxel and then can be measured as exit signal 143 by imaging module 160. Through an iterative approach, the focusing of the imaging signal 123 to a voxel or group of voxels improves over time.

Processing logic 101 has access to the lookup table, and thus, a preferred holographic pattern is linked to each voxel in diffusing medium 130. Then, to image diffusing medium 130, the preferred holographic pattern for each voxel or group of voxels is driven onto display 110 and the exit signal 143 for that voxel is captured by imaging module 160 as an infrared image. Changes to that infrared image for that voxel indicate a change in the voxel or group of voxels. Imaging system 100 cycles through imaging each voxel or group of voxels until each voxel or group of voxels of interest has been scanned. A three-dimensional composite image can be generated by combining the imaged changes of each individual voxel over time. It is noted that once a lookup table is generated that links each voxel or group of voxels to a preferred holographic pattern, using directional ultrasonic emitter 115 or training stimuli are not required to perform the imaging of diffuse medium 130. Furthermore, imaging module 160 doesn't necessarily need to capture the phase of exit signals 143 since the pixel-by-pixel amplitude data for exit signal 143 may be sufficient for detection of changes in voxels.

The changing exit signals 143 for each voxel can show changes over time. Red blood cells are naturally occurring chromophores in that their optical properties correspond to whether the red blood cell is carrying oxygen or not. An oxygen depleted red blood cell will exhibit different optical properties than an oxygen rich red blood cell. Hence, exit signal 143 for each voxel or group of voxels will change based on the level of oxygen in the red blood cells in that voxel. Oxygen consumption in red blood cells corresponds to active areas of the brain. Thus, the active areas of the brain can be known by analyzing the changes in exit signals 143. The active areas in a brain may indicate an injury, inflammation, a growth, a specific thought, or a specific image that someone is recalling, for example. A large change (over time) of exit signals 143 in neighboring voxels could indicate a tumor growth, for example. Additionally, detecting the active areas in particular voxels can be mapped to different actions or thoughts that a person is having, as shown by Dr. Adam T. Eggebrecht of Washington University's School of Medicine in St. Louis, Mo. Dr. Eggebrecht and his co-authors used a Time of Flight measuring optical wig to map brain function in a May 18, 2014 article in Nature Photonics entitled, "Mapping distributed brain function and networks with diffuse optical tomography." This system can detect changes in other chromophores like lipid, melanin, water, and fat, but also directly detect changes in neurons themselves. Active neurons change their light scattering properties through change in membrane potential (a fast transition) or cell swelling (a slow transition). Other optical changes in the body, either via chromophore, scattering changes or phase changes can be detected with this system. With the introduction of fluorescent dyes and particles optical excitation of areas that selectively uptake the wavelength shifting material can be detected by looking for the color shift. All of these beacon indicators can be used with the technique described.

Figure 9:
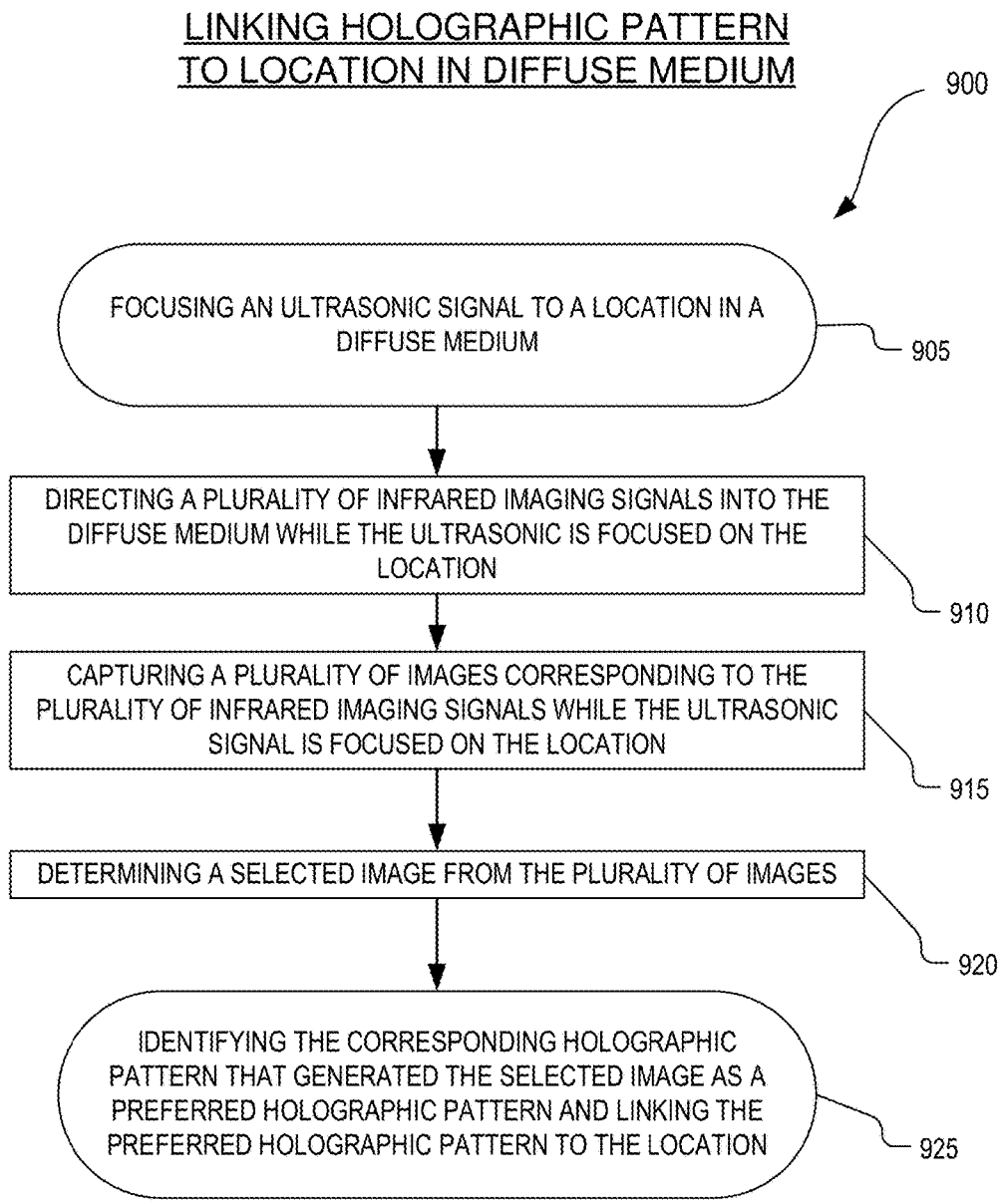
FIG. 9 illustrates an example process of linking a holographic pattern to a location in a diffuse medium, in accordance with an embodiment of the disclosure.

FIG. 9 illustrates an example process 900 of linking a holographic pattern to a location of a diffuse medium that may be performed by imaging system 100 for example, in accordance with embodiments of the disclosure. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel. The instructions for process 900 may be stored in or accessible to processing logic 101 for executing, for example.

In process block 905, an ultrasonic signal (e.g. ultrasonic signal 117) is focused to a location in a diffuse medium (e.g. diffuse medium 130). A plurality of infrared imaging signals is directed into the diffuse medium by driving a corresponding plurality of holographic patterns onto a pixel array (e.g. display 113), in process block 910. The plurality of infrared imaging signals is directed into the diffuse medium while the ultrasonic signal is focused on the location. The plurality of infrared imaging signals (e.g. signal 123) may be directed into the diffuse medium by a holographic display such as display 110.

In process block 915, a plurality of images is captured. The images may be captured by imaging module 160, for example. Each of the images in the plurality captures a corresponding transmission of the plurality of infrared imaging signals directed into the diffuse medium. In other words, a first image in the plurality of images would capture a first transmission of a first infrared imaging signal generated by a first holographic pattern being driven onto the pixel array, a second image in the plurality of images would capture a second transmission of a second infrared imaging signal generated by a second holographic pattern being driven onto the pixel array subsequent to the first holographic pattern being driven onto the pixel array, and so on. As described above, capturing a transmission (e.g. exit signal 143) of an infrared imaging signal while an ultrasonic signal is focused on a voxel allows imaging system 100 to determine which holographic pattern is best suited to image the voxel.

A selected image is determined from the plurality of images by analyzing the plurality of images in process block 920. Each of the plurality of images has a corresponding holographic image pattern. In one embodiment, a phase component of each of the plurality of images is compared to a phase component of a unattentuated image that captured the transmission of an infrared signal generated by the corresponding holographic image pattern when the directional ultrasonic emitter was deactivated. In this way, the phase difference of exit signal 143 can be detected for when the ultrasonic signal is and is not focused on a voxel of a diffuse medium. The analysis of process block 920 may further include determining the selected image by which of the plurality of images had the greatest phase change from its unattentuated image that was captured without the ultrasonic signal 117 being focused on the location.

In process block 925, the holographic pattern that generated the selected image is identified as a preferred holographic pattern and linked to the location. The location and holographic pattern may be stored in a lookup table so that the holographic pattern can be used to image the linked location at a subsequent time.

Process block 925 may be repeated for each voxel of a diffuse medium until each voxel of interest has been linked to a preferred holographic pattern that can be used to generate an infrared holographic imaging signal for imaging the voxel.

Methods that don't use an ultrasonic signal may also be utilized to link a holographic pattern to a location of a diffuse medium. In one embodiment, contrast enhancing injectables or other beacons (e.g. probe) are used to define a certain voxel. Chromophores themselves can also be used as beacons.

Figure 11:
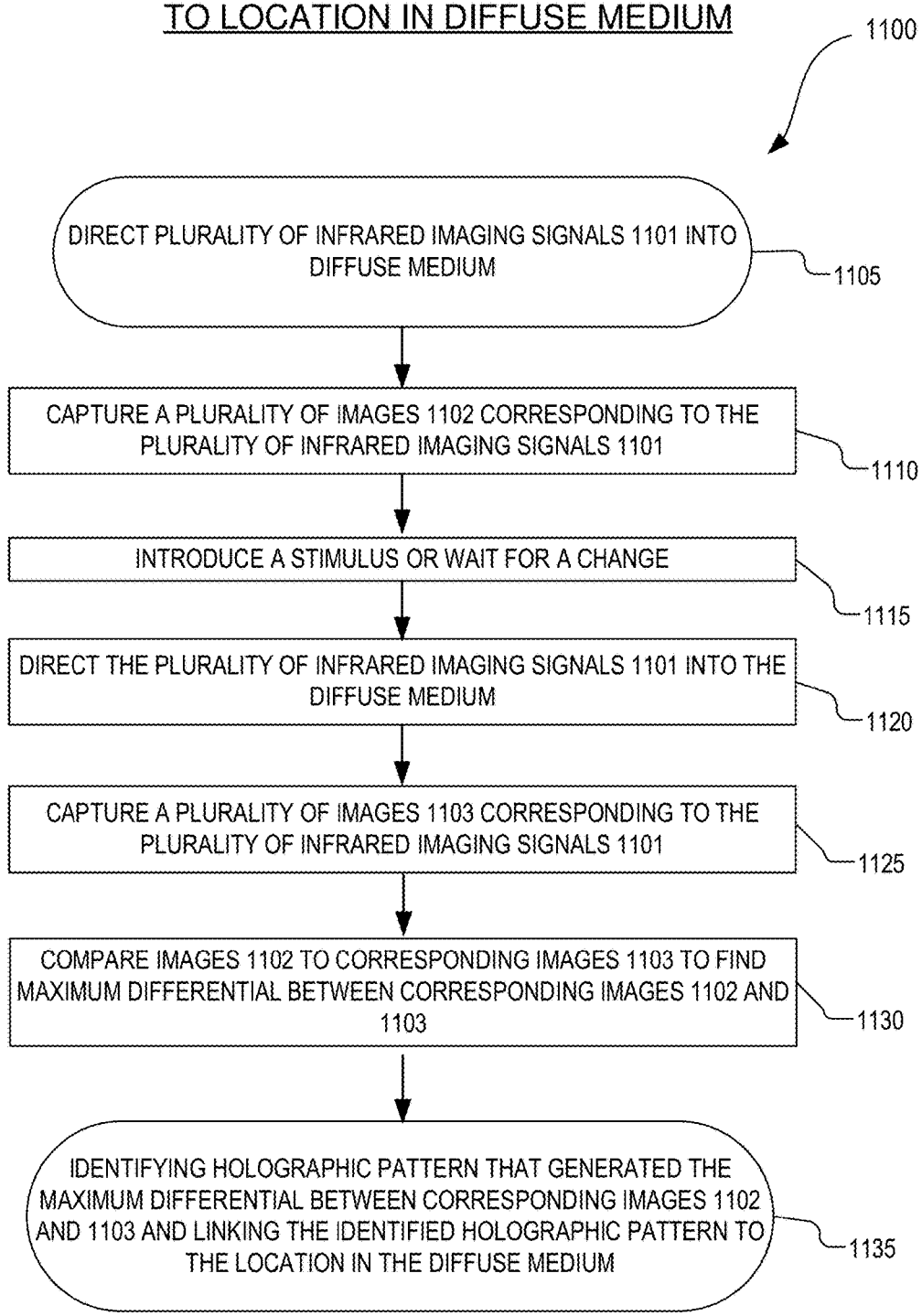
FIG. 11 illustrates an example process of linking a holographic pattern to a location in a diffuse medium, in accordance with an embodiment of the disclosure.

FIG. 11 illustrates an example process 1100 of linking a holographic pattern to a location of a diffuse medium, in accordance with embodiments of the disclosure. Process 1100 may be performed by system 180 or by systems 100 or 200, where directional ultrasonic emitter 115 is optional since process 1100 does not require directional ultrasonic emitter 115. The order in which some or all of the process blocks appear in process 1100 should not be deemed limiting. Rather, one of ordinary skill in the art having the benefit of the present disclosure will understand that some of the process blocks may be executed in a variety of orders not illustrated, or even in parallel. The instructions for process 1100 may be stored in or accessible to processing logic 101/201 for executing, for example.

A plurality of infrared imaging signals 1101 is directed into the diffuse medium by driving a corresponding plurality of holographic patterns onto a pixel array (e.g. display 113), in process block 1105. The plurality of infrared imaging signals (e.g. signal 123) may be directed into the diffuse medium by a holographic display such as display 110.

In process block 1110, a plurality of images 1102 is captured. The images 1102 may be captured by imaging module 160, for example. Each of the images in the plurality of images 1102 captures a corresponding transmission of the plurality of infrared imaging signals 1101 directed into the diffuse medium in process block 1105. In other words, a first image in the plurality of images 1102 would capture a first transmission of a first infrared imaging signal generated by a first holographic pattern being driven onto the pixel array, a second image in the plurality of images would capture a second transmission of a second infrared imaging signal generated by a second holographic pattern being driven onto the pixel array subsequent to the first holographic pattern being driven onto the pixel array, and so on. As described above, capturing a transmission (e.g. exit signal 143) of an infrared imaging signal while a stimulus is first not present and then present allows imaging system 100 to determine which holographic pattern is best suited to image the group of voxels changed by the stimulus.

In process block 1115 a stimulus is introduced or a period of time is allowed to pass. Where the brain is being imaged, the stimulus (e.g. stimulus 197) may be showing an image to a person, playing music for the person, or requesting that the person think of an idea or an image. At process block 1120, the plurality of infrared imaging signals 1101 are directed into the diffuse medium. In process block 1125, a plurality of images 1103 are captured. Each of the images in the plurality of images 1103 captures a corresponding transmission of the plurality of infrared imaging signals 1101 directed into the diffuse medium in process block 1120 while the stimulus of process block 115 is applied or presented.

In process block 1130, corresponding images from the plurality of images 1102 and the plurality of images 1103 are compared to find the maximum differential between corresponding images. Corresponding images from the plurality of images 1102 and 1103 are images that are captured when the same holographic pattern is driven onto the display. Each of the plurality of images has a corresponding holographic image pattern without stimulus applied in the group of images 1102 and with stimulus applied in the group of images 1103. In one embodiment, a phase component of each image from 1103 is compared to a phase component of a corresponding unattentuated image from 1102 that captured the transmission of an infrared signal generated by the corresponding holographic image pattern when no stimulus was presented. In this way, the phase difference of exit signal 143 for a given voxel can be detected for when a stimulus is and is not present. The analysis finding the maximum differential of process block 1130 may further include determining which of the corresponding images from 1102 and 1103 have the largest phase change.

In process block 1135, the holographic pattern that generated the maximum differential in process block 1130 is identified as a preferred holographic pattern and linked to the location/voxel of interest. The location and holographic pattern may be stored in a lookup table so that the holographic pattern can be used to image the linked location at a subsequent time.

Process block 1130 may be repeated for each stimulus of a diffuse medium until the stimulus of interest has been linked to a preferred holographic pattern that can be used to generate an infrared holographic imaging signal for imaging the voxel.

FIG. 2 illustrates an imaging system 200 that includes an integrated module 290A that includes image pixel array 170, filter 173, IR director 103, IR emitter 105, IR display 113, IR director 253, and IR emitter 155. Imaging system 200 also include directional ultrasonic emitter 115 and processing logic 201. Imaging system 200 may also include the wireless transceiver described in system 100 as coupled to processing logic 201. In the illustrated embodiment of integrated module 290A, filter 173 is disposed between IR director 103 and image pixel array 170. IR director 103 is disposed between IR display 113 and filter 173. IR display 113 is disposed between IR director 253 and IR director 103.

Imaging system 200 has similarities to imaging system 100. IR emitter 105 is activated by output X3 of processing logic 201. IR director 103 receives the infrared light from IR emitter 105 and directs the infrared light to IR display 113 as IR wavefront 107 to illuminate IR display 113. A holographic pattern is driven onto IR display 113 to generate an infrared holographic imaging signal 223, which is directed to voxel 133. Signal 223 propagates through voxel 133 and is incident on integrated module 290B as exit signal 273. Integrated module 290B may be the same as integrated module 290A, in FIG. 2. Integrated module 290B includes an image pixel array 170 that images exit signal 273 through IR display 113. The amplitude and phase modulations (if any) of the pixels of IR display 113 within integrated module 290B can be subtracted from the image capture of exit signal 273 by processing logic 201 to determine the actual image of exit signal 273. For example, if a display pixel of IR display 113 within integrated module 290 was driven to cut the amplitude of incident infrared light in half, the image signal generated by exit signal 273 on the image pixel directly behind the display pixel would be multiplied by two to recover the original amplitude of exit signal 273. In one embodiment, the pixel dimensions of display 113 and image pixel array 170 are the same. The phase of the light from the exit signal 273 can be recovered similarly by accounting for the phase shift (if any) that is driven onto display pixels of display 113.

Holographic patterns for driving onto IR display 113 to image different voxels of diffuse medium 130 may be determined similarly to process 900 or 1100. Integrating IR display 113 with the image pixel array 170 in integrated module 290 is potentially advantageous for packaging and form factor reasons, as will be described in connection with FIGS. 4A and 5. Integrated module 290 may also be advantageous because integrated module 290B could both image exit signal 273 and generate its own infrared holographic imaging signal 293 to be sent back to integrated module 290A (as exit signal 243) via voxel 133. In one embodiment, integrated module 290B images exit signal 273 and determines the phase and amplitude of the exit signal 273 using the techniques described above. Since the optical path between integrated modules 290A and 290B is reversible, integrated module 290B may calculate the conjugate of the imaged exit signal 273 and drive the conjugate holographic pattern onto its own IR display 113 to generate its own infrared holographic imaging signal 293 that is directed back to IR display 113 via voxel 133 as exit signal 243. As the infrared holographic imaging signal 293 propagates through diffuse medium 130 in the opposite direction, the phase and amplitude will then match the initial holographic pattern driven onto IR display 113 of integrated module 290A. The image pixel array 170 of integrated module 290A can measure the amplitude and phase of exit signal 243 and compare it to the holographic pattern that was originally driven onto IR display 113. Differences between exit signal 243 and the holographic pattern driven onto IR display 113 can then be detected and analyzed for changes within voxel 133.

Although there will be some movement of the body when system 100 or 200 is imaging, valuable imaging signals can still be obtained since the movement is relatively slow compared to the imaging speed. Movement of the tissue being imaged may come from movement of the head or from a heart pumping blood, or a vein expanding and contracting due to different blood flow, for example. To aid in the imaging, the Memory Effect principles described in Issac Freund's 1988 article entitled, "Memory Effects in Propagation of Optical Waves through Disordered Media" (Rev. Lett 61, 2328, Published Nov. 14, 1988) can be employed. Additionally, big data analytics may be employed to organize the images of voxels into a composite image.

Figure 3:
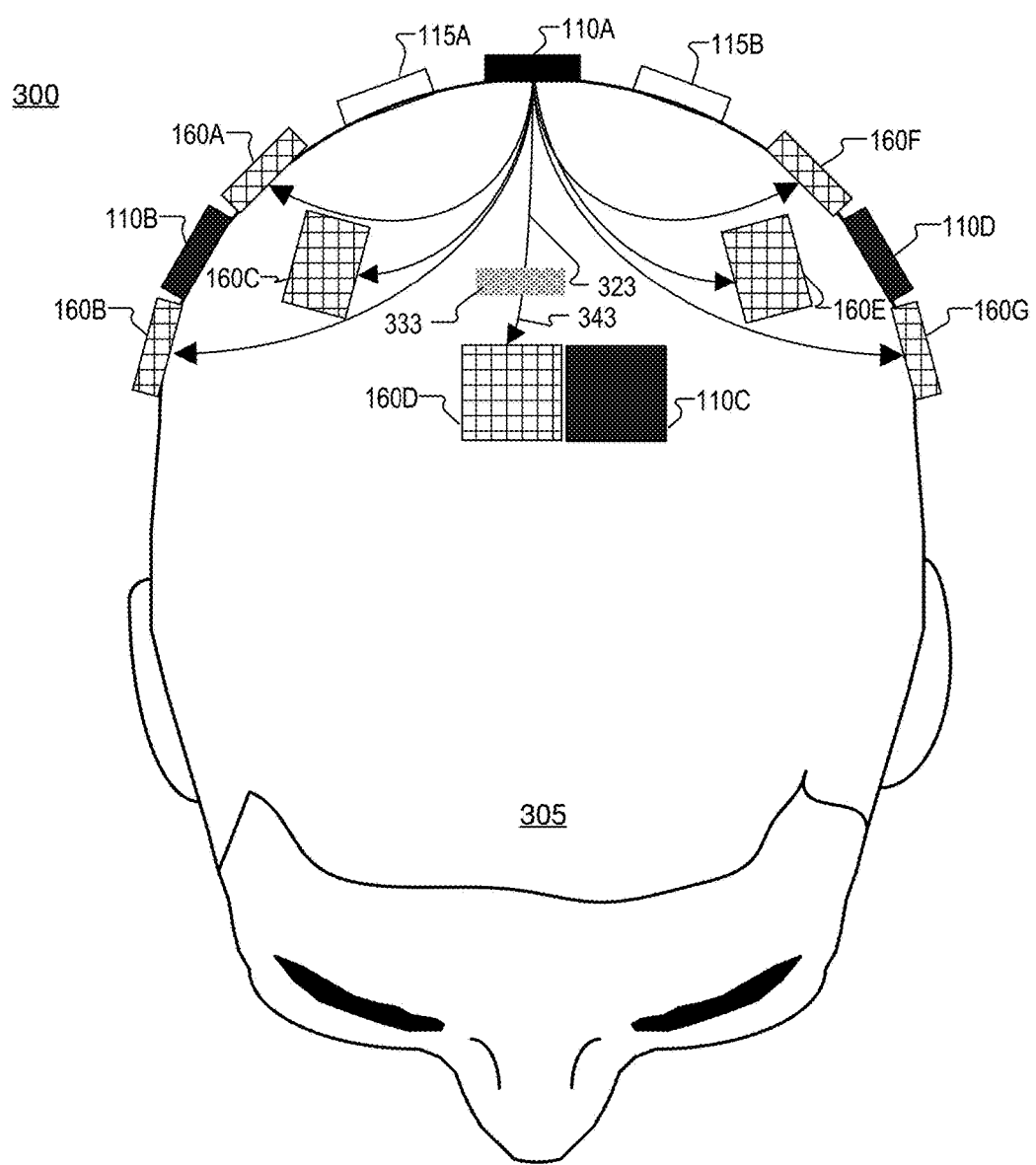
FIG. 3 illustrates example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes display 110A-110D, imaging modules 160A-160F, and directional ultrasonic emitters 115A and 115B. Components 110A-110D and 160A-160F may all be replaced with module(s) 290 which can function as both display 110 and imaging module 160. Displays 110A-110D and imaging modules 160A-F are shown in FIG. 3 although more or less displays and imaging modules may be used in a system. FIG. 3 shows that display 110A may generate multiple holographic infrared imaging signals 323 that are directed to image different voxels 333 of the brain while the exit signals 343 are imaged by different imaging modules 160. FIG. 3 illustrates that display 110A sends an infrared holographic imaging signal to each of imaging modules 160A-F. Not all the voxels, infrared holographic imaging signals, and exit signals are illustrated and referenced in FIG. 3 as to not obscure the description of the system. The other displays 110B-110D may also send infrared holographic imaging signals (not illustrated) to each of imaging modules 160A-F. Scientific literature suggests that the penetration depth of infrared light into tissue is around 10 cm so multiple holographic displays 110 and imaging module 160 may be needed to image the entire brain or other tissue. It is understood that multiple integrated modules 290 could also be strategically placed around head 305 to image head 305.

FIGS. 4A and 4B illustrate example form-factor implementations of a wearable imaging system, in accordance with an embodiment of the disclosure. FIG. 4A includes a wearable imaging system 498 that includes four optional directional ultrasonic emitters 115, five integrated modules 290, and processing logic 401. Processing logic 401 may be implemented similarly to processing logic 101. Wearable imaging system 498 may include a fabric that has the illustrated components embedded into the fabric. The fabric may be in the form of a wrap that can be wrapped around an abdomen or other body area to facilitate imaging those body areas. The fabric may have velcro or other linking mechanism on edges to assist in maintaining a wrapping around a body area.

FIG. 4B includes a wearable imaging system 499 that includes two optional directional ultrasonic emitters, six displays 110, six imaging modules 160, and processing logic 402. Processing logic 402 may be implemented similarly to processing logic 101. Wearable imaging system 499 may include a fabric that has the illustrated components embedded into the fabric. The fabric may be in the form of a wrap that can be wrapped around an abdomen or other body area to facilitate imaging those body areas. The fabric may have velcro or other linking mechanism on edges to assist in maintaining a wrapping around a body area.

Figure 5:
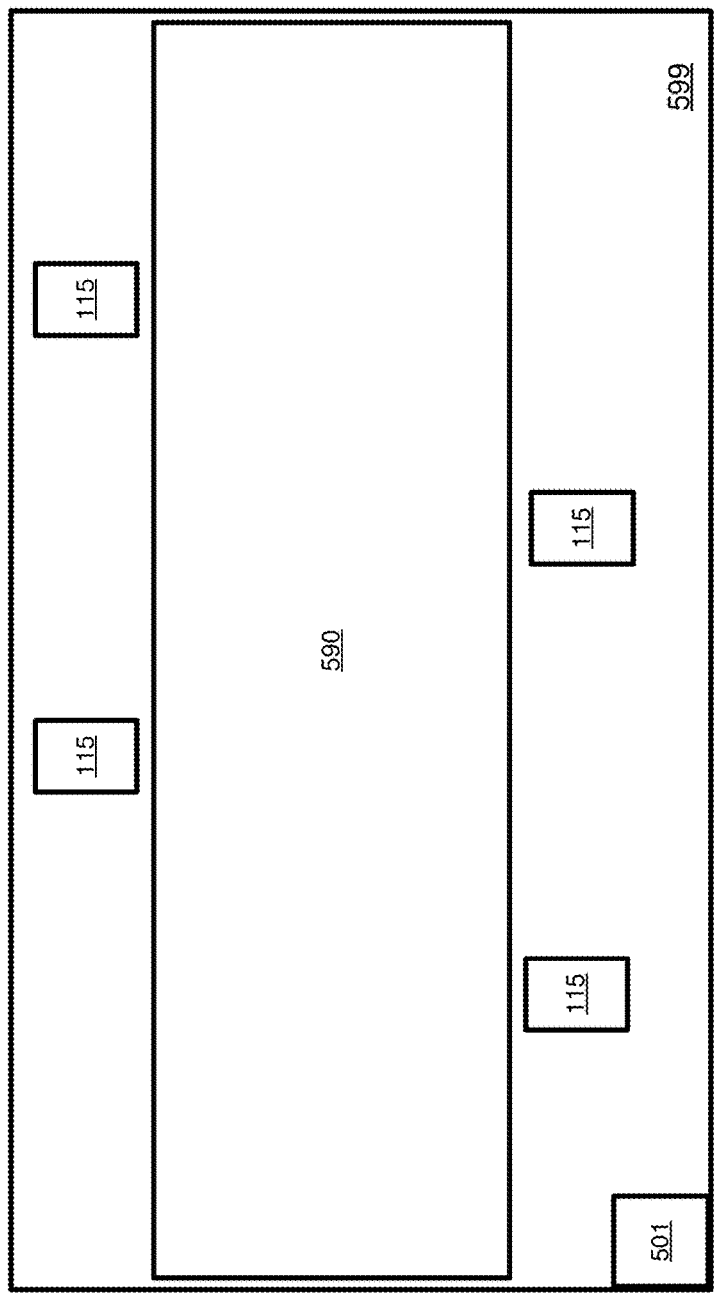
FIG. 5 illustrates an example configuration of a flexible wearable imaging system, in accordance with an embodiment of the disclosure.

FIG. 5 illustrates an example configuration of a flexible wearable imaging system 599, in accordance with an embodiment of the disclosure. Imaging system 599 includes four optional directional ultrasonic emitters, one monolithic integrated module 290, and processing logic 501. Processing logic 501 may be implemented similarly to processing logic 101. Wearable imaging system 599 may include a fabric that has the illustrated components embedded into the fabric. The fabric may be in the form of a wrap that can be wrapped around an abdomen or other body area to facilitate imaging those body areas. The fabric may have velcro or other linking mechanism on edges to assist in maintain a wrapping around a body area. Imaging system 599 is similar to imaging system 498 in that it includes integrated modules. Integrated module 590 is similar to integrated module 290 except that integrated module 590 is built with flexible components so that integrated module 590 can be monolithic and therefore provide a large-area holographic display and large-area imaging module in one component that would be potentially less expensive to manufacture. Flexible LCD technology is used for the holographic display for example. It is understood that batteries, power regulators, and other required components of imaging systems 498, 499, and 599 are not illustrated so as not to obscure the Figures of the disclosure.

Figure 6:
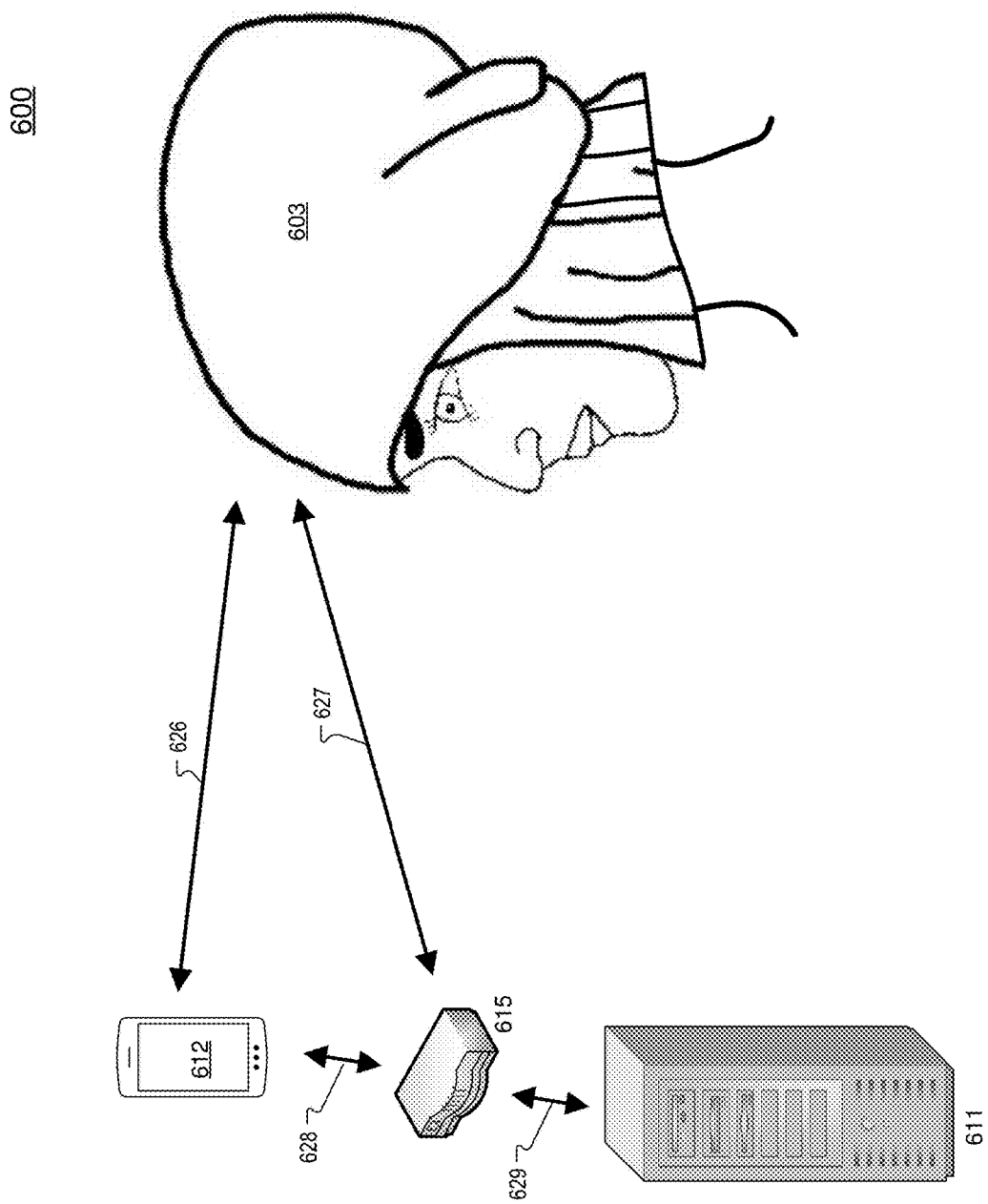
FIG. 6 illustrates a networked system in communication with an example wearable imaging system for being worn on or about a head, in accordance with an embodiment of the disclosure.

FIG. 6 illustrates a networked system 600 in communication with an example wearable imaging system for being worn on or about a head, in accordance with an embodiment of the disclosure. System 600 includes a ski-cap wearable 603 that is being worn on the head of a user. Systems 100, 200, 300, 498, 499, and/or 599 may be included in wearable 603. Wearable 603 includes wired or wireless network connections to router 615 and/or mobile device 612 (e.g. smartphone or tablet). The communication channel 626 between wearable 603 and mobile device 612 may be BlueTooth™ or WiFi utilizing IEEE 802.11 protocols, for example. The communication channel 627 between wearable 603 and router 615 may use a wired Ethernet connection or WiFi utilizing IEEE 802.11 protocols, for example. Mobile device 612 may also communicate with wearable 603 via communication channels 628 and communication channel 627. Mobile device 612 may give the users some results or alerts about the imaging being performed by wearable 603. Router 615 may also route data from wearable 603 to a computer 611 via communication channel 629. Computer 611 may function as a server, in some embodiments. Computer 611 may give medical professionals access to the imaging of the user's brain by wearable 603, for example.

In one embodiment, processing intensive algorithms are performed by computer or server 611. For example, process 900 or 1100, image processing algorithms, and simulated annealing algorithms described above may be performed by computer 611. In this case, the imaging modules of the systems may capture the images and send the raw data to computer 611 for further processing. Computer 611 may then report the results of the processing back to wearable 603 for local storage. Mobile device 612 may perform similar "off-site" processing for wearable 603.

The techniques described in this disclosure have been described largely in the context of medical imaging. However, the uses of the methods, systems, and devices are not so limited. In one embodiment, imaging small voxels of the brain is used as a way to discern thoughts. Different thoughts and images correspond to different blood usage by neurons (as shown by Dr. Eggebrecht and his co-authors, and others) which can be imaged by the systems, devices, and methods described herein. Discerning (even rudimentary) human thought can be used to assist quadriplegics and others who don't have full functionality of their extremities. Imaging their thoughts could allow for translating their thoughts into a mechanical action (e.g. driving a wheelchair forward or typing words). In one implementation, a user recalls (thinks about) an image of a forward arrow. Imaging system 100, 200 or 280 images the brain and records a voxel pattern that is known to be linked to the forward arrow recalled by the user. When imaging system 100, 200, or 280 images the forward arrow thought pattern, it generates an additional action (e.g. rolling wheel chair forward or typing an "up arrow" on a keyboard).

In one use contemplated by the disclosure, sending infrared light to specific voxels of the brain is used as a therapy. In some cancer treatments, binding agents are ingested or injected, where the binding agents are targeted to selectively bind to tumors. Once the binding agents are bound to the tumor, the described systems could activate the binding agent by selectively exciting the binding agent with infrared light (on a voxel-by-voxel basis), for example. In another use contemplated by the disclosure, the described systems are used in the field of optogenetics—to change the state of neurons with light therapy. Changing the state of neurons with light therapy allows for stimulation of areas of the brain that may otherwise require a physical fiber optic probe being inserted. Light therapy can be used for treatment and research for autism, Schizophrenia, drug abuse, anxiety, and depression, for example. Changing the state of neurons with light therapy may also allow for images or other information to be imparted to the brain, which may be especially useful for patients with memory loss.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A medical imaging device comprising:
    processing logic;
    an emitter for emitting infrared light within a frequency band;
    a display pixel array including a plurality of pixels, each pixel in the plurality of pixels is individually configurable to modulate an amplitude of the infrared light received from the emitter to generate an infrared holographic imaging signal according to a holographic pattern driven onto the display pixel array by the processing logic; and
    an image pixel array including a plurality of imaging pixels configured to receive incident light within the frequency band and reject light outside of the frequency band, the processing logic coupled to the image pixel array to initiate a capture of an infrared image, wherein the processing logic is further coupled to receive the captured infrared image from the image pixel array.

2. The medical imaging device of claim 1 further comprising:
    a reference wavefront generator configured to illuminate the image pixel array with a reference wavefront in response to receiving an activation signal generated by the processing logic, the processing logic causing the reference wavefront generator to illuminate the image pixel array during a time period overlapping with the capturing of the infrared image by the image pixel array, wherein the reference wavefront is within the frequency band.

3. The medical imaging device of claim 2, wherein the reference wavefront generator receives the infrared light from the emitter, and wherein the emitter is a laser and the frequency band is monochromatic infrared light.

4. The medical imaging device of claim 1 further comprising:
    a directional ultrasonic emitter configured to dynamically focus an ultrasonic signal to a given voxel in three-dimensional space, wherein the processing logic is configured to drive the directional ultrasonic emitter to focus the ultrasonic signal to a first voxel in three-dimensional space while also driving the holographic pattern onto the display pixel array and while initiating the capture of the infrared image with the image pixel array.

5. The medical imaging device of claim 1, wherein the image pixel array is positioned to image an exit signal generated by the infrared holographic imaging signal propagating through a diffuse medium.

6. The medical imaging device of claim 1, wherein the incident light received by the image pixel array passes through the display pixel array before being incident on the image pixel array.

7. The medical imaging device of claim 1, wherein a pixel pitch of the display pixel array is less than or equal to five times the wavelength of the monochromatic infrared light.

8. The medical imaging device of claim 1, wherein the display pixel array is included in a holographic display and each pixel in the display pixel array is independently configurable to modulate a phase of the infrared light received from the emitter.

9. The medical imaging device of claim 8, wherein modulating the phase of the infrared light for each of the pixels in the plurality of pixels includes driving a voltage across two electrodes of the pixel to align liquid crystal between the two electrodes to change a length of an optical path of the infrared light propagating through the pixel in order to achieve a specified phase of the infrared light as it exits the pixel.

10. A method of imaging tissue, the method comprising:
    illuminating a display pixel array with an infrared wavefront within a frequency band;
    forming an infrared holographic imaging signal by driving a holographic pattern onto the display pixel array while the display pixel array is illuminated by the infrared wavefront;
    capturing an infrared image by measuring the amplitude of an exit signal with pixels of an image pixel array, the exit signal generated by the infrared holographic imaging signal propagating in the tissue, wherein the pixels of the image pixel array are configured to receive light within the frequency band and reject light outside the frequency band; and
    generating a compostie image of the tissue, wherein the composite image includes the infrared image captured by the image pixel array and additional infrared images captured by the image pixel array while corresponding additional holographic patterns are driven onto the display pixel array.

11. The method of claim 10 further comprising:
    directing a reference wavefront to the image pixel array and capturing the infrared image while the reference wavefront is incident on the image pixel array; and
    calculating a phase of the exit signal.

12. The method of claim 10, wherein the holographic pattern is configured to direct the infrared holographic imaging signal to the image pixel array via propagation through a voxel in the tissue, wherein the holographic pattern is linked to the voxel.

13. The method of claim 12 further comprising:
    determining a difference between the infrared image and a prior infrared image that was captured by the image pixel array while the holographic pattern was driven onto the display pixel array during a past time period.

14. The method of claim 12 further comprising:
    selecting a second holographic pattern associated with a second voxel;
    forming a second infrared holographic imaging signal by driving the second holographic pattern onto the display pixel array; and
    capturing a second infrared image by measuring a second exit signals with the image pixel array, wherein the second exit signal is generated by the second infrared holographic imaging signal propagating through the second voxel in the tissue.

15. The method of claim 10, wherein a pixel pitch of the display pixel array is less than or equal to five times the wavelength of the infrared wavefront.

16. A method comprising:
focusing an ultrasonic signal to a location in tissue;
directing a plurality of infrared imaging signals into the tissue by driving a corresponding plurality of holographic patterns onto a pixel array, the plurality of infrared imaging signals directed into the tissue while the ultrasonic signal is focused on the location;
capturing a plurality of images, wherein each of the plurality of images captures a corresponding transmission of the plurality of infrared imaging signals directed into the tissue while the ultrasonic signal is focused on the location;
selecting a preferred holographic pattern from the plurality of holographic patterns; and
generating a composite image of the tissue, wherein generating the composite image of the tissue includes driving the preferred holographic pattern onto the pixel array when the ultrasonic signal is not focused on the location in the tissue.

17. The method of claim 16, wherein focusing the ultrasonic signal includes:
directing an ultrasonic signal to a membrane; and
driving an electronic signal to the membrane to shape the membrane to focus the ultrasonic signal to the location.

18. The method of claim 16 further comprising:
linking, in a computer-readable medium, the preferred holographic pattern to the location.

* * * * *